(12) United States Patent
Yaddgo et al.

(10) Patent No.: US 6,381,981 B1
(45) Date of Patent: May 7, 2002

(54) CONTAINER FOR SHIPPING AND STORING FROZEN PRODUCTS

(75) Inventors: Jerry Yaddgo, Lakeside; Stephen Kemmerrer, San Diego; Charles Bankert, Oceanside, all of CA (US)

(73) Assignee: Advanced Tissue Sciences, Inc., La Jolla, CA (US)

( * ) Notice: Subject to any disclaimer, the term of this patent is extended or adjusted under 35 U.S.C. 154(b) by 0 days.

(21) Appl. No.: 09/847,902

(22) Filed: May 2, 2001

(51) Int. Cl.7 .................................................. F25D 3/08
(52) U.S. Cl. ....................................... 62/372; 62/457.2
(58) Field of Search ............................... 62/239, 457.1, 62/457.2, 372, 457.7; 220/559, 578

(56) References Cited

U.S. PATENT DOCUMENTS

| | | | | |
|---|---|---|---|---|
| 3,164,289 A | * | 1/1965 | Cocchiarella | 220/578 |
| 3,654,773 A | * | 4/1972 | White | 220/23.87 |
| 5,520,014 A | * | 5/1996 | Laugier | 62/457.2 |
| 5,689,970 A | * | 11/1997 | Chopas | 62/372 |
| 5,711,164 A | * | 1/1998 | Slack | 62/237 |
| 6,269,285 B1 | * | 7/2001 | Mignault | 206/745 |

* cited by examiner

Primary Examiner—William E. Tapolcai
Assistant Examiner—Mohammad M Ali
(74) Attorney, Agent, or Firm—Pennie & Edmonds LLP

(57) ABSTRACT

The present invention is directed to a container and method for shipping and storing frozen products. In particular, the present invention is directed to an insulated container for shipping and storing frozen tissue samples for an extended period of time, for example at least 72 hours. An exemplary embodiment of the container of the present invention includes a body having an open end and a product chamber lined with vacuum insulated panels, a spring assembly inside of the product chamber for supporting a lower cooling block and a stack of tissue packages (e.g. engineered tissue samples), and a lid assembly including one or more upper cooling blocks suspended therefrom. When the lid assembly is secured on the body of the container, the tissue packages are held in place between the upper and lower cooling blocks by the force of the spring assembly. The body of the container is dimensioned so that it may fit within an outer cardboard carton if desired for shipping.

57 Claims, 11 Drawing Sheets

CONTAINER FOR SHIPPING AND STORING FROZEN PRODUCTS

TECHNICAL FIELD

The present invention relates generally to a container for shipping and storing temperature-sensitive products, and in particular to a container for maintaining frozen tissues and other products during shipping and storage.

BACKGROUND OF THE INVENTION

Currently available containers for transporting frozen or refrigerated products generally include a cardboard shipping carton lined with insulating material such as such as expanded polystyrene (EPS), polyurethane or other foam material. The insulating material may be in the shape of modular panels or, for example, may be injection molded into any desired shape. The insulation typically defines a central cavity where products are stored along with a coolant, such as ice packs or loose blocks of dry ice. A plug, such as a thick polyester or polyether foam pad, is generally placed over the top of the product before the carton is closed and prepared for shipping.

Such conventional shipping containers have many limitations, particularly when shipping or storing sensitive frozen products, such as sterile frozen tissue samples, for extended periods of time. For example, engineered tissue implants, must be maintained in a sterile condition at or below approximately −65° C. for a number of days during transcontinental or international shipping, particularly in the case of shipping delays or extended storage. Conventional containers simply are not adequately insulated or designed to maintain such products at low temperatures for more than one or two days. While increasing the thickness and/or number of layers of insulating material may aid in extending product maintenance time, the resulting increase in size and cost of such a shipping container is typically prohibitive.

Another problem with conventional shipping containers is that they fail to provide constant, evenly distributed contact between coolant and product. Such constant contact and even distribution of the coolant is desirable for maintaining frozen products over an extended period of time. In typical shipping containers, however, products and/or coolant blocks often shift during shipping and handling, resulting in a loss of contact or a change in the distribution of coolant. Such shifting is increasingly problematic during extended periods when the coolant decreases in size as it melts or sublimates, or if a recipient removes a portion of the product and wishes to maintain the rest in the container. Shifting of contents during transport may also result in damage to the product, its packaging or labeling, and may compromise product sterility. Additionally, in situations where a coolant block is placed on top of a product, conventional containers require a recipient to handle the block to access the product, possibly resulting in injury to the recipient or damage to the product.

Accordingly, there remains a need in the art for a improved container for shipping and storing varying amounts of frozen products at low temperatures for extended periods of time, while minimizing overall size and weight of the container.

SUMMARY OF THE INVENTION

The present invention is directed to a container for shipping and storing frozen products. In particular the present invention is directed to an insulated container for shipping and storing frozen tissue samples for an extended period of time. An exemplary embodiment of the container of the present invention includes a body having an open end and a product chamber, a spring assembly inside of the product chamber for supporting a cooling block and one or more packages of tissue (e.g. engineered tissue samples), and a lid assembly including one or more cooling blocks suspended therefrom that contact at least one of the tissue packages when the lid assembly is placed over the open end of the container body. The body of the container is dimensioned to fit within an outer container for shipping.

In the above-described exemplary embodiment, the body of the container includes an inner container and an outer container. The outer container is in the shape of an open box, with four side walls and a bottom lid of insulated foam material, such as EPS, polyurethane or any other rigid or soft foam. The inner surface of the walls and bottom of the outer container are lined with four vacuum insulated side panels and a bottom panel that comprise the inner container and define the product chamber. In certain embodiments, the outer and/or inner container have more than four walls, such that the body and/or product chamber is hexagonal, octagonal or the like. In certain other embodiments, the outer and/or inner containers may have less than four walls, such that the body and/or product chamber is triangular, cylindrical, elliptical, etc.

In an exemplary embodiment, a gasket is disposed between the bottom edge of the side panels and the bottom panel to reduce air flow in or out of the chamber. Adjacent side panel are beveled to ensure a tight seal. Optionally, panels may be configured, attached or sealed in any manner to minimize leaks between adjacent panels. Optionally, the product chamber is lined with a single or double layer of corrugated cardboard or similar material to protect the vacuum panels.

The spring assembly of this exemplary embodiment fits in the bottom of the product chamber and has a resilient spring member disposed between two plates, a bottom plate and a top plate. The bottom plate rests against, and is optionally attached to, the bottom of the product chamber. The top plate faces the open end of the chamber, and is adapted to support the lower cooling block and the stack of tissue samples. A clip is added to the top plate to maintain the coolant on the center of the product. The clip anchors and positions the coolant on the center/main mass of the product and prevents the coolant from shifting, particularly when the shipper is laid on its side. When the lid assembly is placed over the body, the stack of tissue samples is held between the upper and lower cooling blocks by the force of the spring. The spring has enough travel to assure forceful contact regardless of the quantity of product being shipped and to allow for sublimation of the dry ice during shipping and storage. In an alternative embodiment, the spring assembly is positioned above the product, for example it may be attached to the lid assembly.

The lid assembly of the above-described exemplary embodiment includes a top lid, a top vacuum panel, and a restraint for suspending the upper cooling block(s). When placed over the body, the restraint is disposed within the product chamber, the top panel mates with the inner chamber, and the top lid mates with the outer chamber. The elements of the lid assembly are attached for ease of removal, such that a recipient of the container need not touch the cooling blocks to access the tissue samples. A strap is optionally provided to aid in the removal of the lid assembly.

BRIEF DESCRIPTION OF THE DRAWINGS

For a better understanding of the nature and details of the invention, reference should be made to the following detailed description taken in conjunction with the accompanying drawings, in which.

Like reference numerals refer to corresponding parts throughout the several views of the drawings.

DESCRIPTION OF THE INVENTION

Figure 1:
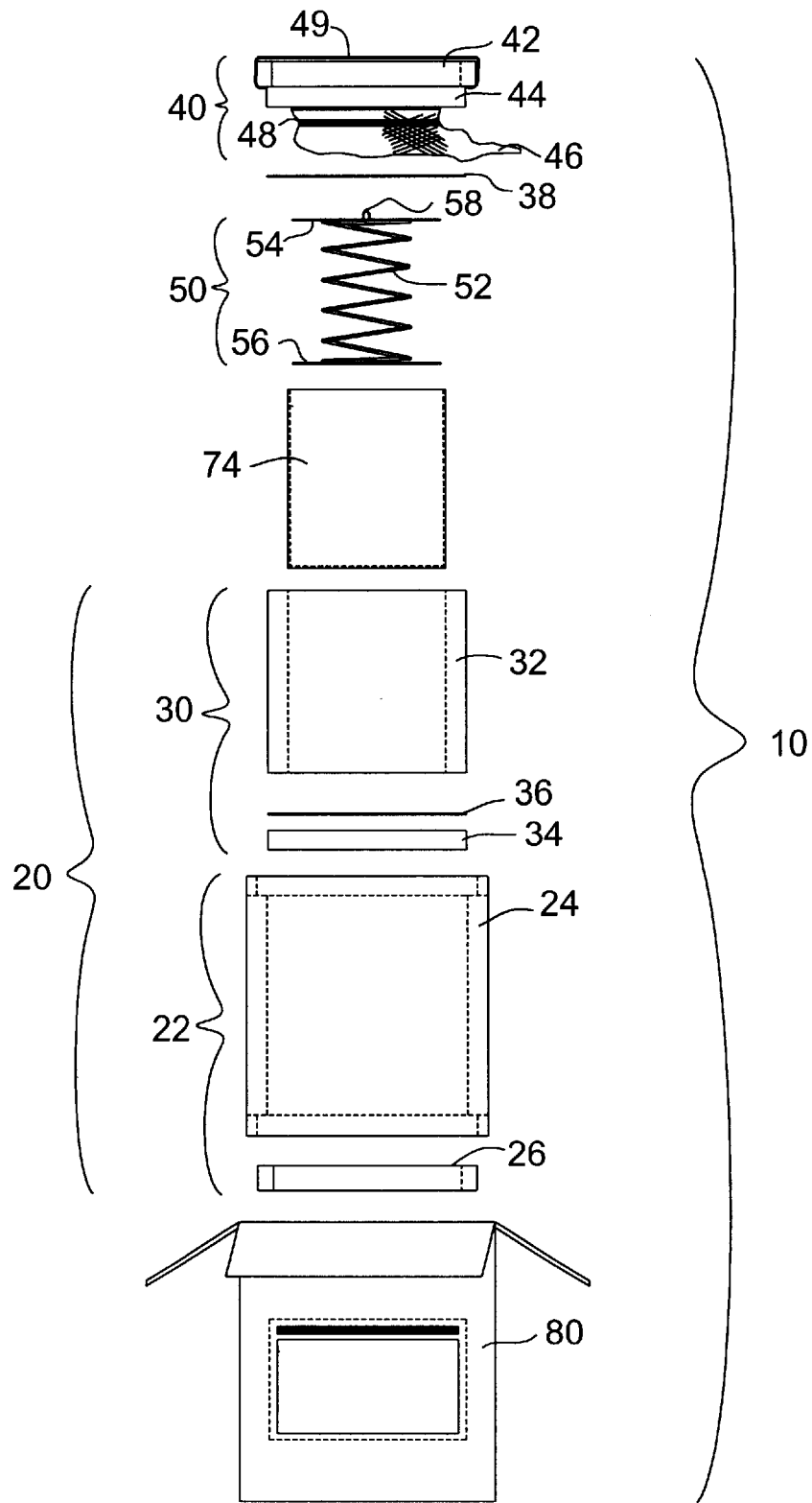
FIG. 1 is an exploded side view of an exemplary embodiment of the shipping container of the present invention.
Figure 2A:
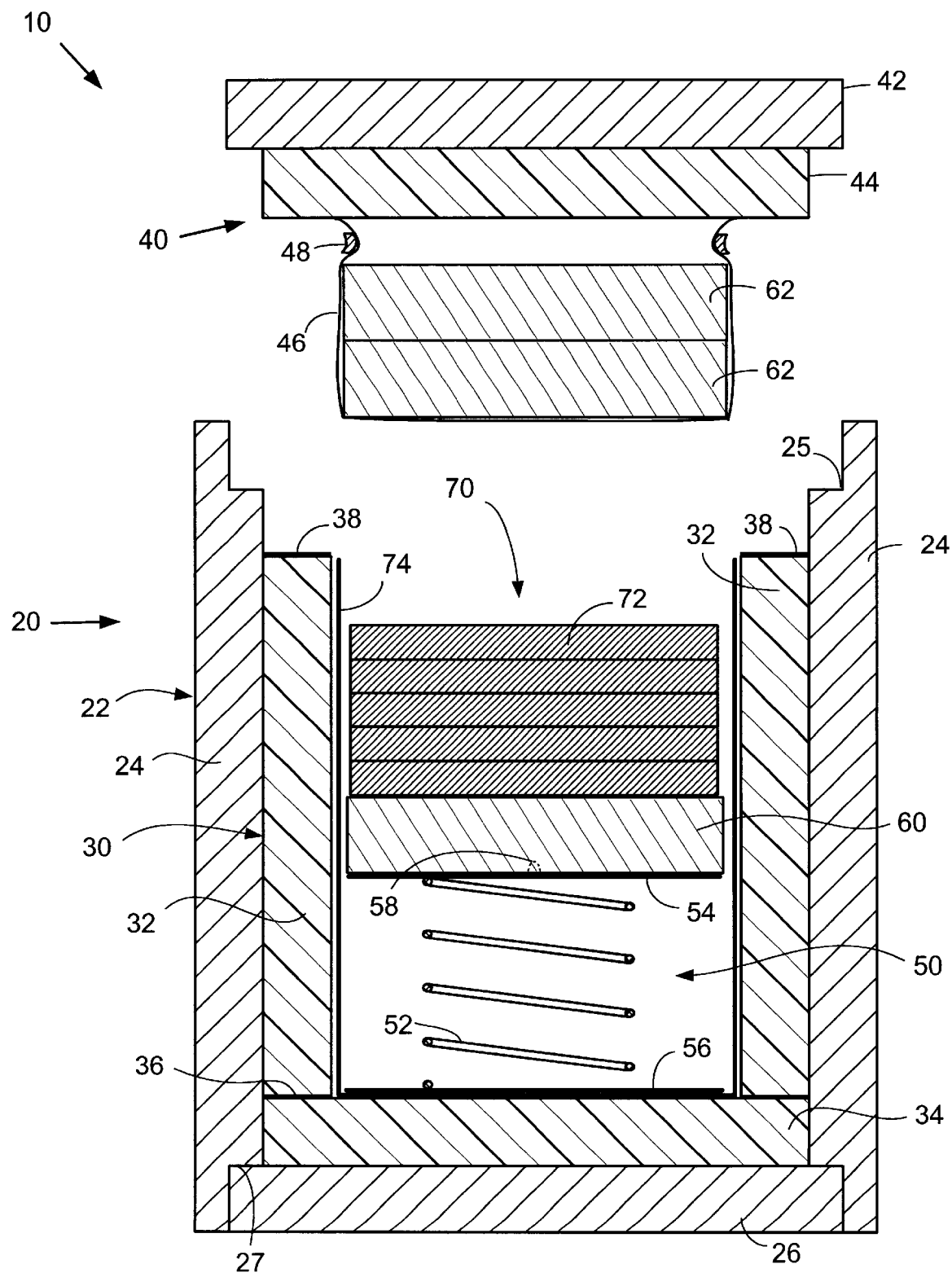
FIG. 2A is a cross-sectional side view of the shipping container of FIG. 1, shown in an open configuration.
Figure 2B:
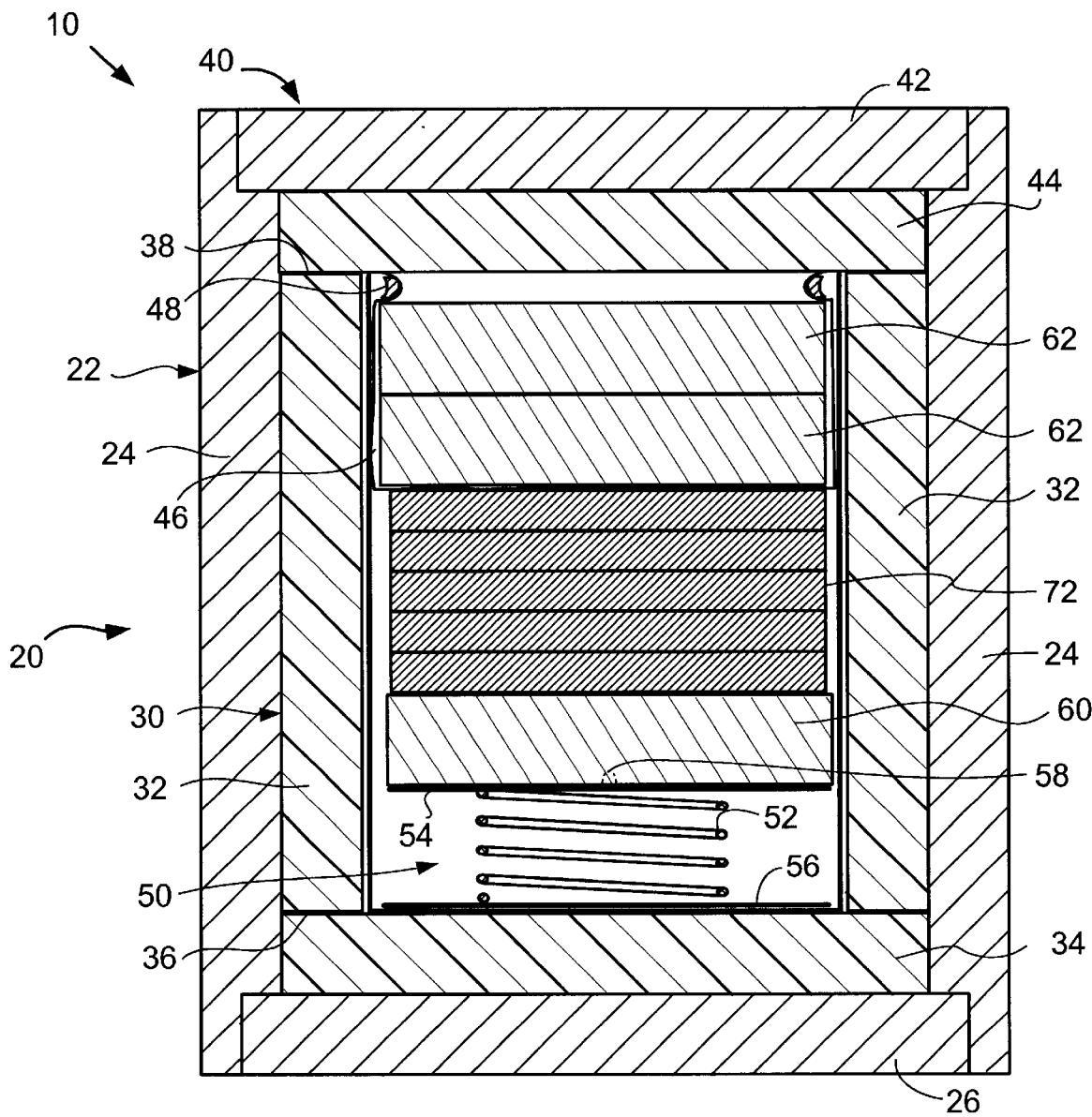
FIG. 2B is a cross-sectional side view of the shipping container of FIG. 1, shown in a closed configuration.

FIGS. 1 and 2 show an exemplary embodiment of a container 10 for shipping frozen tissues according to the present invention. Container 10 generally includes a body 20, a spring assembly 50, a lid assembly 40 and an outer carton 80. As best shown in FIG. 2A, body 20 includes an open product chamber 70 for holding spring assembly 50, one or more products 72 (e.g. packages of frozen tissue), and one or more cooling members, or blocks 60. Lid assembly also includes one or more cooling blocks 62 suspended within a restraint 46. When lid assembly is placed over the open end of container body 20 as shown in FIG. 2B, product 72 is held tightly between upper cooling block 62 and lower cooling block 60 by a biasing force of spring assembly 50. Upper cooling block 62 and lower cooling block 60 are both typically, although not necessarily, dry ice.

Container body 20 includes an outer container 22 and an inner container 30. Outer container 22 has four side walls 24 and a bottom lid 26, arranged to form the shape of an open square or rectangular box. Alternatively, outer container 22 may have any number of side walls arranged to form any desired shape, such as a cylinder. Side walls 24 and bottom lid 26 are constructed of styrofoam panels that are dimensioned and arranged to line the interior of carton 80. In certain embodiments, side walls 24 and bottom lid 26 are interlocking expanded polystyrene (EPS) panels having a thickness of 0.5 to 2.0 inches. In other embodiments, the thickness is about 1.0 inch. Alternatively, polyurethane foam or other material having suitable insulating properties may be used to line carton 80 and form outer container 22. As is best shown in FIG. 2A, each side wall 24 includes notches 25, 27 along its upper edge and lower edge, respectively. When side walls 24 are fitted together, notches 27 form a ledge that is dimensioned to mate with bottom lid 26, and notches 25 form a ledge that is dimensioned to mate with lid assembly 40. One skilled in the art will appreciate that the walls 24 may be dimensioned and configured in various ways to line the interior of carton 80 without departing from the scope of the invention. For example, in an alternative embodiment of the invention, outer container 22 is a single body comprised of side walls and a bottom wall constructed of injection molded EPS (not shown).

Referring again to FIG. 2A, inner container 30 is comprised of four side panels 32 and a bottom panel 34 that line the interior surfaces of outer container 22 and define product chamber 70. Panels 32 and 34 are insulated panels such as vacuum insulated panels comprising a core material (e.g. DOW INSTILL HT, INSTILL UC, INSTILL AF or similar core material) and a barrier film (e.g. a mylar barrier film such as DUPONT MYLAR 22RS BL300, MYLAR 250 RS BL300, MYLAR 350 RS BL300, or similar material). Panels 32 and 34 of the present embodiment have a thickness of approximately 1.0 inch, but other thicknesses (e.g., 0.25–2.0 inches) may be used depending upon the desired insulation properties and overall size and weight of container 10. Each side panel 32 may be beveled along its side edges (not shown) to form a tight joint between adjacent panels. One skilled in the art will appreciate that adjacent panels may be connected or joined in any manner to ensure a tight seal, and may be dimensioned and arranged in any fashion to give the product chamber a desired size and shape.

Optionally, a thin gasket 36 is disposed between the bottom end of each side panel 32 and bottom panel 34, as shown in FIGS. 2A and 2B. Gasket 36 is shaped and dimensioned in any fashion suitable for creating a seal between panels 32 and 34, such as a rectangular ring. Gasket 36 is comprised of polyethylene or any other compressible material suitable for creating a seal between panels 32 and 34 in order to limit air flow into an out of chamber 70.

Body 20 of shipping container 10 optionally includes a protective liner 74 inside chamber 70 to protect panels 32 and 34 from contact by spring assembly 50, product packages 72, cooling blocks 60, 62 or other contents of chamber 70. Protective liner may be of any material suitable for protecting panels and/or providing additional insulation, such as single or double-walled corrugated cardboard or foam.

Like body 20, lid assembly 40 generally comprises two layers of insulating material: top lid 42 and top panel 44. Top lid 42 is configured and dimensioned essentially the same as bottom lid 26, and is comprised of the same material as outer container 22 (e.g., EPS foam or other foam material). One or more corners 43 of lid 42 may be cut or notched to facilitate removal of lid assembly 40.

Top panel 44 is a vacuum panel comprised of the same material as inner container 30 (e.g., DOW INSTILL core material with DUPONT mylar polyester barrier films as described above) and dimensioned approximately the same as bottom panel 34. Top lid 42 and top panel 44 are attached together, for example by adhesive material such as tape, glue or epoxy or by straps, staples, screws or any other attachment means. In an alternative embodiment of the shipping container of the present invention, top lid and top panel are not attached together. In yet another alternative embodiment, top lid and top panel are not distinct elements, rather lid assembly is comprised of a single injection molded top lid having shaped plug (not shown) that fits within cavity 70 when the lid assembly is placed on body 20.

A cooling block restraint 46, such as a net comprised of polyethylene, nylon or other suitable material, is attached to lid assembly 40. Restraint may be secured between top panel 44 and top lid 42, or may be attached directly to top panel 44 or top lid 42 using any suitable adhesive or other attachment means, such as tape, glue, epoxy, staples, brads, screws, etc. Restraint 46 is of such size and strength as to hold one or more cooling blocks 62 (e.g. dry ice) suspended from lid assembly 22 when assembly 22 is removed from body 20 of container 10. For example, the embodiment of FIGS. 1 and 2 uses an approximately 24 inch, heat-sealed polyethylene net 46 (NSW Corporation, Roanoke, Va.).

A band 48, such as a band of rubber, silicone or other elastic material, is placed around net 46 and cooling blocks 62 to gather any excess material and prevent it from interfering with the seal between lid assembly 40 and body 20 when container 10 is closed. Band 48 also aids in centering upper blocks 62 over product 72 within chamber 70. Restraint 46 allows a customer or other user of shipping container to access product 72 without handling cooling blocks 62. Restraint 46 also ensures replacement of upper cooling blocks 62 when lid is returned, thereby ensuring that thermal performance of container 10 is maintained for continued storage of any remaining any product 72.

As shown in FIG. 1, a strap 49 is optionally attached to lid assembly 40 to facilitate placement and removal of lid assembly. For example, strap 49 may be a loop of nylon, cotton, rubber, plastic or any other material of suitable strength wrapped around top lid and/or secured between top lid and top panel.

Lower block 60 and upper blocks 62 of FIGS. 2A and 2B are typically dry ice, for example, with dimensions of approximately 5"×7"×1.7". However, one skilled in the art will appreciate that various sizes and numbers of blocks may be used depending, for example, upon the size and characteristics of the shipping container, the 20 type and amount of product to be shipped or stored, the desired temperature of the product and the desired duration of storage. Alternatively, other cooling elements, such as ice bags, gel packs, freezer blocks, liquid nitrogen containers, or the like may be used.

Spring assembly 50 includes a spring member 52 disposed between top plate 54 and bottom plate 56. Spring member 52 is a coil compression spring constructed of metal, plastic, or other material. In an exemplary embodiment, spring member 52 is a 0.135" wire compression spring having an outside diameter of approximately 4.25", a free length of approximately 7.0" and a fully compressed height of less than 1.0" under a load of 12–15 lbs. Naturally, other spring sizes and configurations may be used without departing from the scope of the invention. Similarly, the strength of spring member 52 may vary depending, at least in part, upon the size of the container, the amount of product to be shipped and/or stored, and the weight of the cooling blocks.

One skilled in the art will appreciate that maximum load of spring member 52 generally should be greater than the weight of the contents of the container (e.g. product 72 plus cooling blocks 60, 62), however not so great as to damage product 72 or prevent sealing of container 10 when lid assembly 40 is placed on body 20. Other suitable types of springs include, but are not limited to, compression and extension springs, constant force wire springs, wave, finger and curved springs, die springs, Belleville disc springs and torsion springs. Alternatively, other devices or material having resilient qualities may be used in place of spring assembly 50.

Top plate 54 and bottom plate 56 are typically relatively flat plates attached to either end of spring member 52 and dimensioned to fit within chamber 70 when spring assembly is placed vertically in chamber 70. Plates 54 and 56 aid in keeping spring assembly 50 centered in chamber 70, provide a stable surface for supporting cooling block 60 and product 72, and ensure that spring 52 delivers a parallel force. Plates 54 and 56 may be constructed of any rigid material such as cardboard, plastic, metal, wood, etc.

Top plate 54 typically includes a locating clip 58 extending upward from its approximate center. Locating clip 58 is comprised of wire, nail, wood, plastic or other material shaped to anchor cooling block 60. In certain embodiments, block 60 includes a matching hole (not shown) that fits over locating clip 58 when block 60 is placed on spring assembly 50. In use, locating clip 58 aids in keeping block 60 centered over top plate 54, particularly when container 10 is placed on its side. Bottom plate 56 is secured, using adhesive, tape, glue, staples, tabs, or any other attachment means to bottom of chamber 70.

Outer carton 80 of FIG. 1 is typically a corrugated box such as a single or double walled corrugated box. Carton 80 includes fasteners, such as tape or re-usable hook and loop fasteners (i.e. Velcro), to counteract the force of spring assembly 50 and ensure a tight seal between lid assembly 40 and body 20, particularly between top panel 44 and side panels 32. Reusable Velcro fasteners are advantageous because they tend to be effective even after repeated uses, allowing re-sealing of container 10 after it is opened.

When lid assembly 40 is placed on body 20 as shown in FIG. 2B, upper cooling blocks 62 and restraint 46 enter product chamber 70 while top lid 42 mates with walls 24 of outer container 22 and top panel 44 mates with side panels 32 of inner container 30. Gasket 38 aids in creating a seal between top panel 44 and side panels 32. Closing and securing carton 80 with fasteners ensures a tight seal between lid assembly 40 and body 20, particularly between top panel 44 and side panels 32. Optionally, fasteners on lid assembly (not shown) are used to secure lid assembly 40 in place on body 20.

With lid assembly 40 in place and carton 80 secured, upper cooling block 62 contacts the upper surface of product 72 and compresses spring member 52. Compressed spring member 52 forces lower cooling block 60 and product 72 toward upper cooling block 62 and ensures secure contact between product 72 and blocks 60 and 62. Such contact is maintained even as container 10 is shifted or placed on its side and/or as cooling blocks 60, 62 shrink in size. Moreover, even after a portion of product 72 is removed and container 10 is resealed, spring assembly 50 forces lower cooling block 60 and remaining product 72 toward upper cooling block 62 such that remaining product 72 again is forcefully held between upper 62 and lower 60 cooling blocks. Spring assembly 50 also serves to act as a shock absorber, protecting product 72 and its packaging from being damaged due to shock or vibration during shipping and handling.

As stated above, the shipping container of the present invention is capable of maintaining tissues and other temperature sensitive products at a temperature of −65° C. or less for extended periods of time. The vacuum panels 32, 34 and 44 of inner container 30 allow so little radiant thermal loss that the primary dry ice mass loss is due to sublimation. This means that the shape of blocks 60 and 62 shrink in a relatively dimensionally stable, constant ratio manner, thus maximizing the contact area between blocks 60, 62, and product 72, and maintaining the desired product temperature.

One skilled in the art will appreciate that container 10 of FIGS. 1 and 2 is an exemplary embodiment incorporating various aspects of the present invention, and the particular combination and arrangement of the components is not intended to be limiting thereof. For example, spring assembly 50 may be attached to lid assembly or placed in container on top of one or more upper cooling blocks 62. In such a configuration, placing lid assembly 40 on body 20 compresses spring assembly 50 and forces product toward bottom of container (i.e. panel 34 and bottom lid 26). Alternatively, two or more spring assemblies may be used on opposite sides of product 72.

Figure 3:
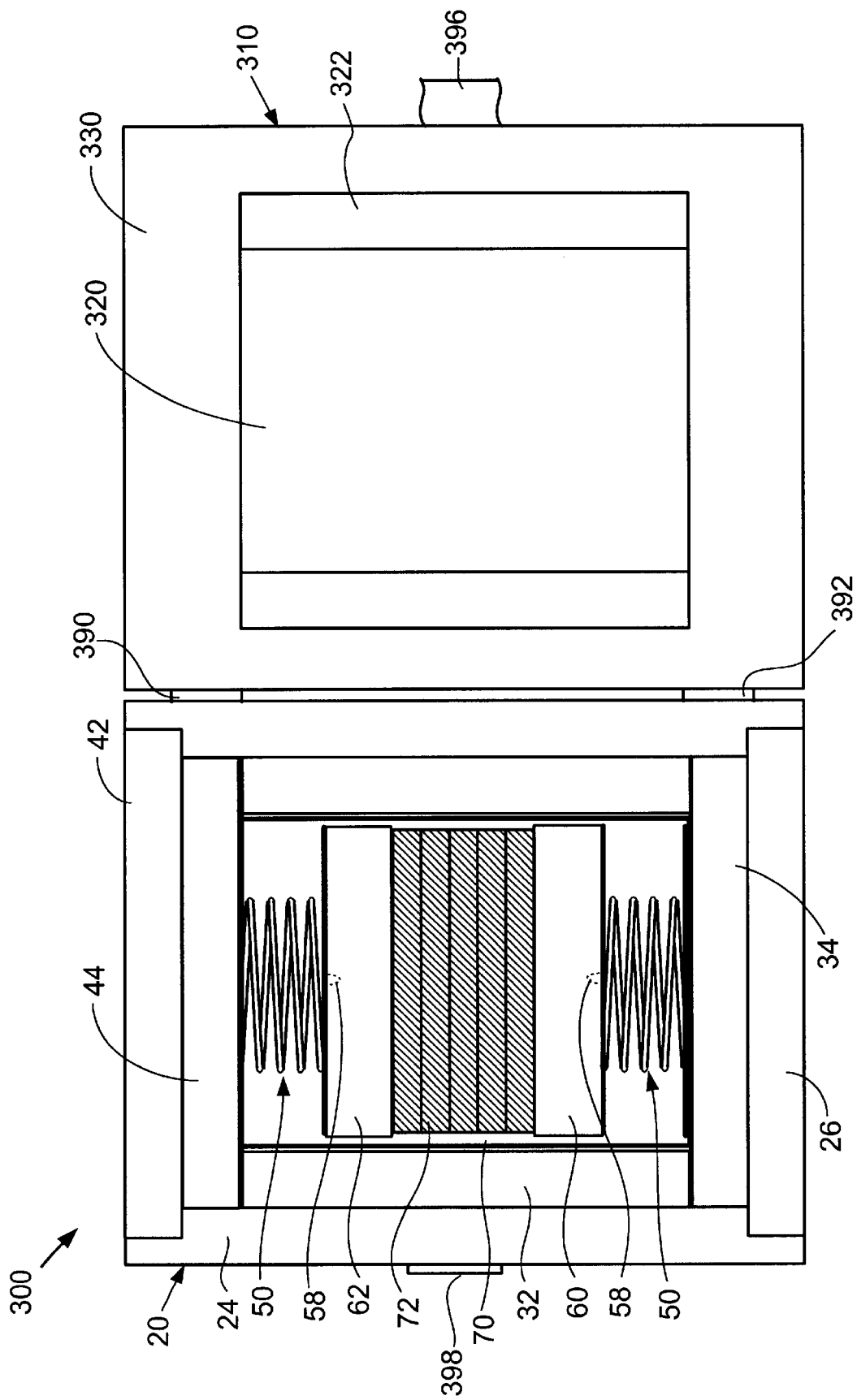
FIG. 3 is side view of an alternative embodiment of a shipping container according to the present invention.

Container 300 of FIG. 3 is another exemplary embodiment of the shipping container of the present invention. Some of the components of container 300 are essentially the same as container 10, however container 300 includes a door assembly 310 for accessing product 72 and a second spring assembly 50 disposed between product 72 and top panel 44. Container 300 does not include cooling block restraint 46 of FIGS. 1–2 as lid assembly 40 (i.e. top lid 42 and top panel 44) is not removed to access product as in FIG. 2A. Rather, door assembly 310 is attached to body 20 by straps, hinges or the like such that door assembly 310 may be opened or removed from body 20 to access product 72. In the exemplary container 300, straps 390, 392 hingably attach door assembly 310 to body 20 and strap 396 removably secures door assembly 310 to body 20 when closed. One skilled in the art will appreciate that a variety of means of securing door assembly 310 to body 20 may be used in order to facilitate opening and closing of door assembly 310.

Door assembly 310 comprised of door wall 330, which is similar to side walls 24, and door panel 320, which is similar to side panels 32. In certain embodiments, door panel 320 has beveled edges 322 configured to mate with the edges of side panels 32 when door assembly 310 is closed. Door panel 320 is dimensioned such that it enters product chamber 70 and fits between upper panel 44 and lower panel 34 when door assembly 310 is closed.

In an alternative embodiment of container 10 of FIGS. 2A–B, restraint 46 is not used and lid assembly hingably attaches (not shown) to body 20 like door assembly 300 of FIG. 3. In such an embodiment, one or more spring assemblies 50 are oriented in product chamber 70 orthogonally to the open end of body 20, similar to the orientation of spring assemblies 50 in container 300 of FIG. 3.

It should be noted that while the exemplary containers 10 and 300 of FIGS. 1–3 are in the shape of a six-sided box, other shapes and/or sizes may be used without departing from the scope of the invention. For example, the container 10 may be in the shape of a hexagon, octagon, rectangle, cylinder, sphere, ellipsoid, or any other shape suitable for a particular application. Moreover, the shape of the product chamber 70 need not correspond to the external shape of the body 20 of the container, e.g. a container having a rectangular body may include a cylindrical product chamber.

The following examples demonstrate the thermal performance and efficacy of exemplary containers constructed and used according to the present invention.

EXAMPLES

Figure 5:
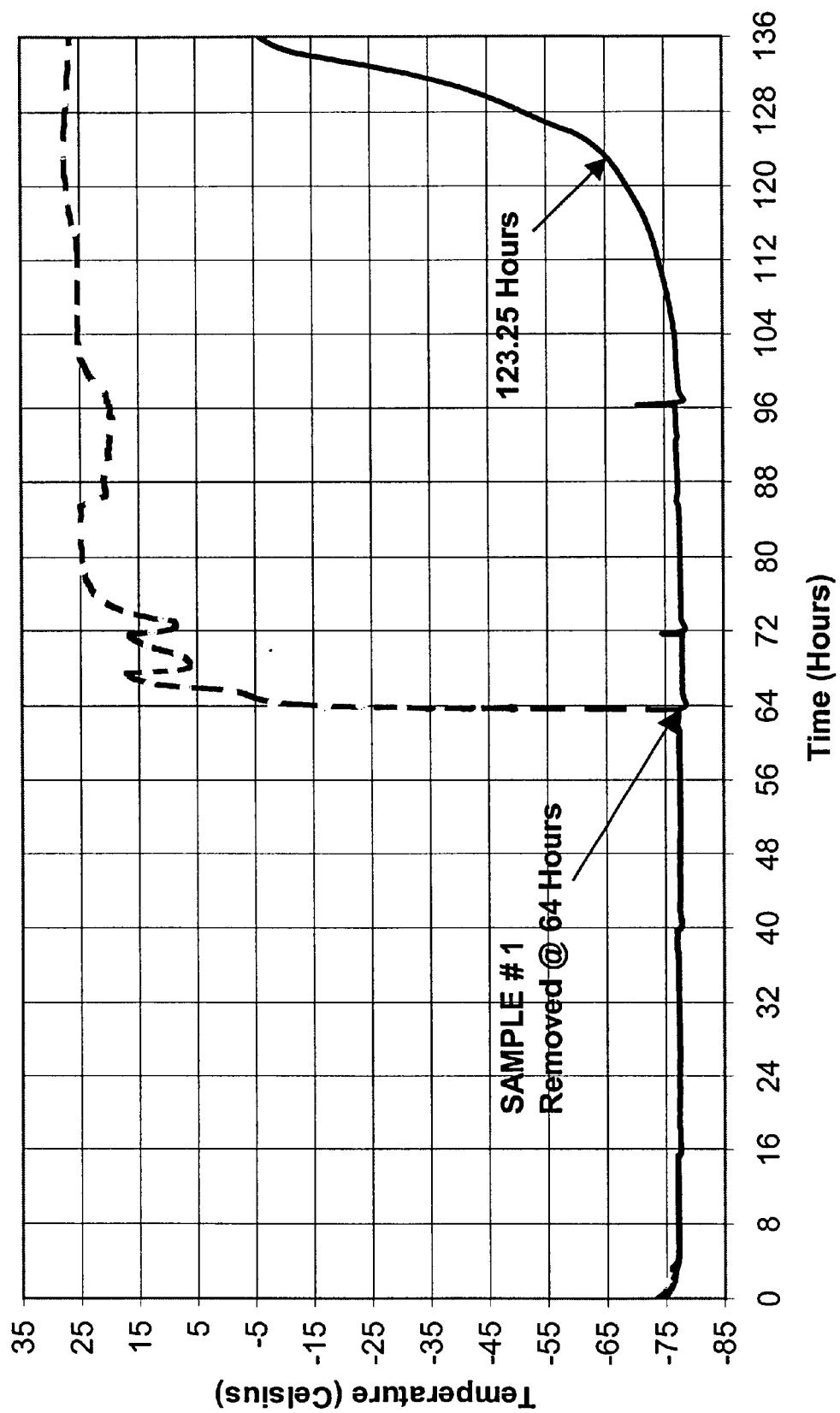
FIG. 5 is a graph showing results of a cooler test of an exemplary shipping container according to FIG. 1.
Figure 6:
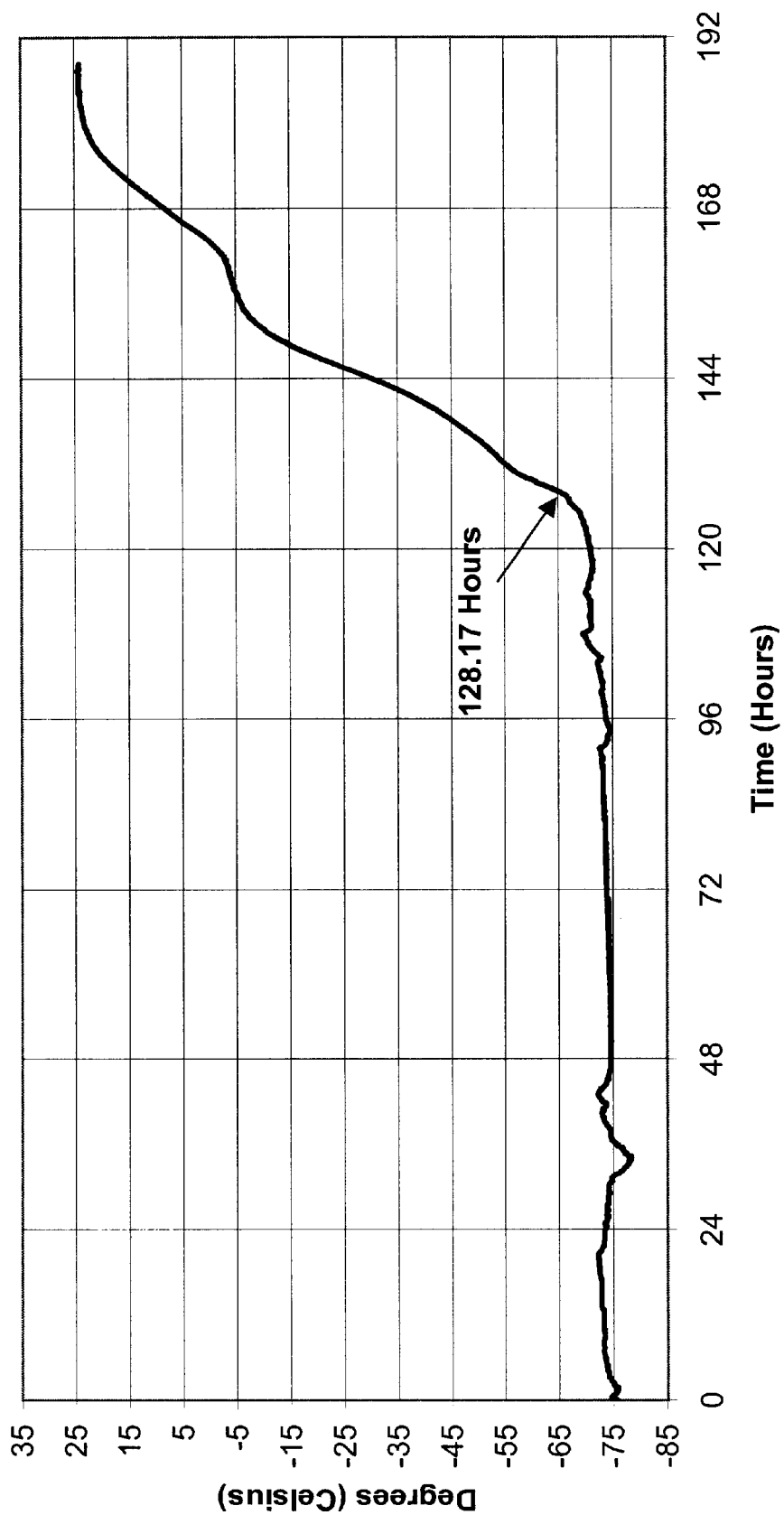
FIG. 6 is a graph showing results of a shock and vibration test of an exemplary shipping container according to FIG. 1.

Three different types of tests were performed on exemplary container 10 of FIGS. 1 and 2 of the present invention to determine the ability of container 10 to safely maintain up to five pieces of simulated frozen product 72 for an extended period of time. These tests included a thermal bench test (FIG. 4), a cooler simulation test (FIG. 5), and a drop and vibration test (FIG. 6). The methods and results of each test are described in more detail below. In all three tests, container 10 was arranged as shown in FIGS. 1 and 2, including body 20 (having outer styrofoam container 22 and inner vacuum panel container 30), lid assembly 40, spring assembly 50, and shipping carton 80. Spring member 52 was a 0.135" (0.34 cm) wire compression spring having an outside diameter of 4.25" (10.80 cm), a free length of 7.0" (17.78 cm) and a fully compressed height of less than 1.0" (2.54 cm). Maximum compression load of spring 52 was approximately 14.5 lbs (6.6 Kg).

In addition to the three tests described above, a series of design tests were performed to determine the effect of different components of the container of the present invention. In particular, these 'design tests' examined the differential and cumulative effects of a spring assembly (e.g. spring assembly 50), vacuum panels (e.g. panels 32, 34 and 44 of container 10 as shown in FIGS. 1 and 2) and/or periodic rotation on performance of a conventional shipping container. Results of the design tests are shown in FIGS. 7–10 and described in more detail below. Essentially, the tests confirm that a shipping container constructed and used according to the present invention yields improved viability of frozen products for extended durations as compared to conventional shipping containers.

The methods and sample results of each of the thermal bench tests, cooler tests, shock and vibration tests, and design tests are described in more detail in the following sections A–D, respectively.

Figure 4:
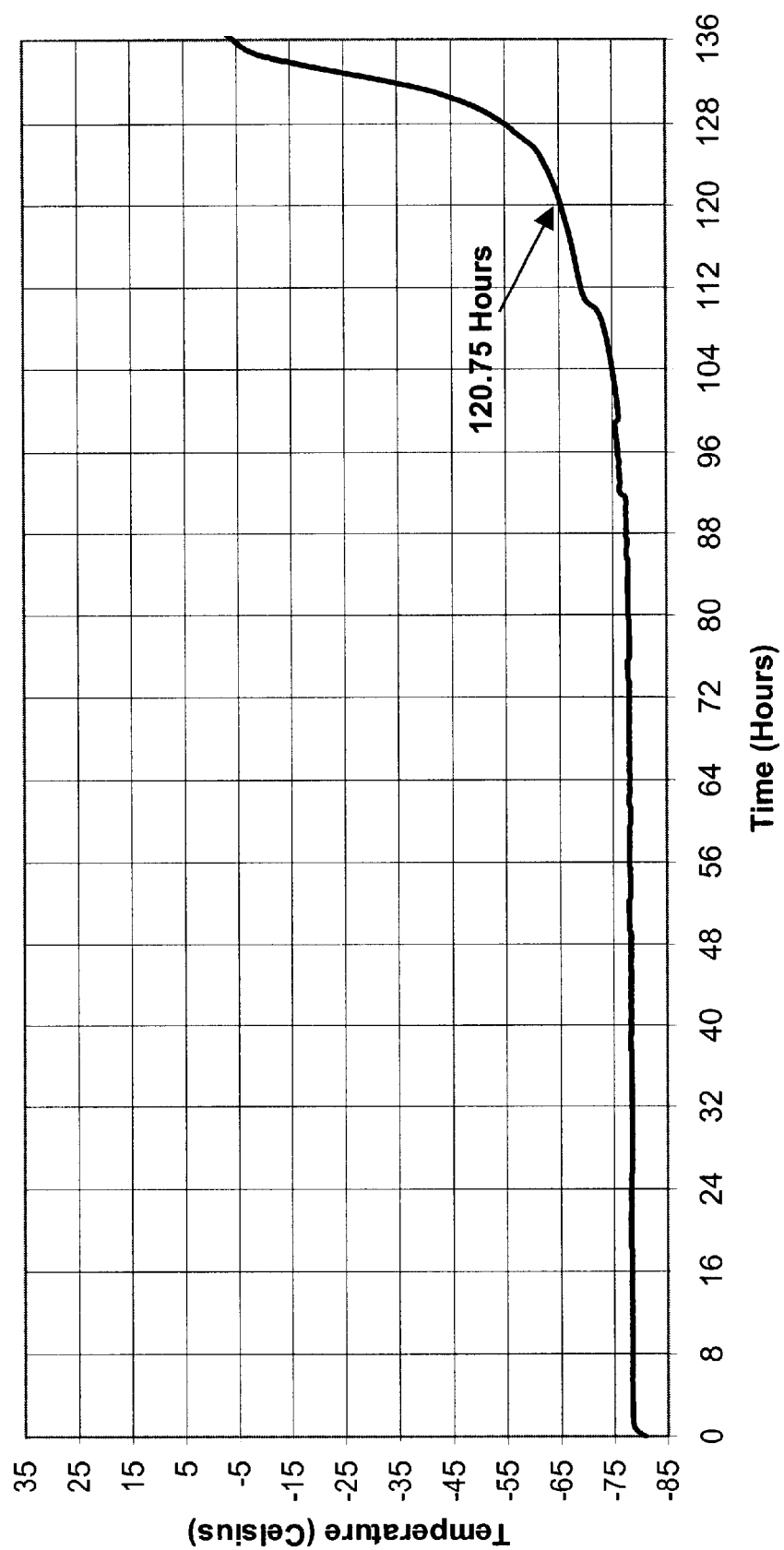
FIG. 4 is a graph showing results of a thermal bench test of an exemplary shipping container according to FIG. 1.

A. Thermal Bench Test (FIG. 4)

The purpose of the thermal bench test was to simulate and evaluate the performance of a shipping container of the present invention when product is shipped but not used by the customer and returned to stock. In such situations, product would be acceptable for restock if the design of the container were suitable for maintaining frozen product for extended periods, e.g. 72 hours or more, and if the container had not been damaged or opened. During the test, a minimum of two containers, similar to container 10, were placed inside an environmental chamber 'incubator' and tested to determine the time required for the product to reach its maximum specified temperature limit, generally −65° C. The first container contained one piece of simulated product and the second container contained five pieces. Three blocks of dry ice were used in each container, one below the product and two above, as shown in FIGS. 2A and 2B. A total dry ice weight of 3.6 Kg was used in each container (approximately 10% below a preferred minimum weight of 4.0 Kg). The containers were subjected to a shipping profile as outlined in Table 1.

TABLE 1

Thermal Bench Test Parameters

| | Out-Bound Shipment Simulation | Dr.'s Office Simulation | In-Bound Shipment Simulation |
|---|---|---|---|
| Transit | 24 hr. Shipment | 24 hr. hold | 24 hr Shipment, test to failure |
| Orientation | Rotate box every 4 hr. ± 1 hr., dice method | Upright | Rotate box every 4 hr. ± 1 hr., dice method |
| Incubator Temp. | 38° C. ± 3° C. | 25° C. ± 3° C. | 38° C. ± 3° C. |

One calibrated thermocouple probe was placed in the first shipper and three thermocouple probes were placed in the second shipper (within the top, center, and bottom simulated product pieces) to measure temperature of the simulated products. The probes were placed inside a media pouch of the simulated products. The incubator had at least two thermocouples to measure temperature of the simulated external environment.

The "dice method" of Table 1 above, refers to a method of labeling each container in a fashion similar to a six-sided playing die. The labeling of the containers in this fashion facilitates the rotation and tracking of the shipping container sides during the tests.

During the thermal bench test, the cooler test, and the vibration test, the simulated product temperatures were required to be below −65° C. for at least 72 hours. Transient temperature excursions above −65° C. were deemed acceptable so long as exposure to room temperature did not exceed 15 seconds. All environmental temperatures were required to be within ±3° C. of their set point during steady state.

FIG. 4 shows the results of a representative thermal bench test of a container according to the present invention having one piece of simulated product as measured by a thermocouple. Product temperature in 0° C. is represented as a solid line. Product temperature was maintained below the target temperature of −65° C. for more than 120 hours, far exceeding the required 'return to stock' time of 72 hours.

B. Cooler Test (FIG. 5)

The purpose of the cooler test was to simulate and evaluate the performance of a shipping container according to the present invention when a product is shipped to the customer and the container is used as a cooler to store the product, for example in a doctor's office. During the test, a minimum of three shippers were placed inside the environmental chamber 'incubator' and tested to determine the time required for product to reach its maximum specified temperature limit (e.g., −65° C.). Each container contained five pieces of simulated product. Calibrated thermocouples were placed in the product and the incubator as described above. The containers used in the cooler test were similar to container 10, and were subjected to a shipping profile as outlined in Table 2.

TABLE 2

| Cooler Test | | |
|---|---|---|
| | Out-Bound Shipment Simulation | Dr.'s Office Simulation (Cooler Test) Test to Failure |
| Transit | 4, 24, 48 hr shipment times | Dr.'s office, 68, 48, 24 hr hold cooler minimum times. |
| Orientation | Rotate box every 4 hr. ± 1 hr., dice method | Upright |
| Incubator Temp. | 38° C. ± 3° C. | 25° C. ± 3° C. |
| Pull Pieces | None | 1st piece at end of transit time, last at failure. Pieces 2, 3 and 4 must have a minimum 4 hr interval between removal. |

FIG. 5 is a graph showing results of a representative cooler test. Samples 2, 3 and 4 (not shown) were removed from the container between 4 and 64 hours, with at least a 4 hour interval between each removal. The temperature of Sample 1 (thick broken line) increased when removed from the container at 64 hours. Sample 5 (thick solid line) remained below −65° C. for over 123 hours, even with the periodic opening of the container and removal of simulated product.

C. Drop and Vibration Test (FIG. 6)

The purpose of the drop and vibration test was to verify that the integrity of the product and its packaging is not damaged by shock and/or vibration during shipping and handling of a container according to the present invention. For this test, two shipping containers were tested for shock and vibration per the International Safe Transit Association (ISTA) standards (ISTA 1A and 1C ). The first container contained one simulated product piece and the second contained five pieces. The temperature of at least one piece of simulated product was monitored as described above. The testing profile is outlined in Table 3.

TABLE 3

| Drop and Vibration Test Shipping Parameters | | |
|---|---|---|
| | Out-Bound Shipment Simulation | ISTA Shock and Vibration Test |
| Transit | 24 hr. Shipment | Performed between 24 and 72 hr |
| Orientation | Rotate box every 4 hr. ± 1 hr., dice method | Per ISTA Test |
| Incubator Temp. | 38° C. ± 3° C. | Per ISTA Test |

Following the test, the containers were opened after failure (96+ hours) and inspected for damage to the container and/or the simulated product. No such damaged was found. As shown in FIG. 6, the temperature of one of the product remained at or below −65° C. for over 128 hours during the test.

D. Design Tests (FIGS. 7–10)

As mentioned above, several variations of a shipping container of the present invention were tested for their ability to maintain five pieces of simulated product at a temperature of −65° C. or lower for an extended period of time under a number of different conditions. In particular, these 'design tests' examined the effects of vacuum panels, a spring assembly, and periodic rotation or movement of a container. For each test, a thermocouple probe was placed within each of the five pieces of simulated product. During testing, each container was maintained in an incubator at 38° C.±3° C. The results of each design test are shown in FIGS. 7–10, where the temperature of each simulated product is represented by a separate thick solid line. Each graph includes a notation of the elapsed the time when a first product exceeded a temperature of −65° C.

Design Test 1: Conventional Shipping Container

Figure 7:
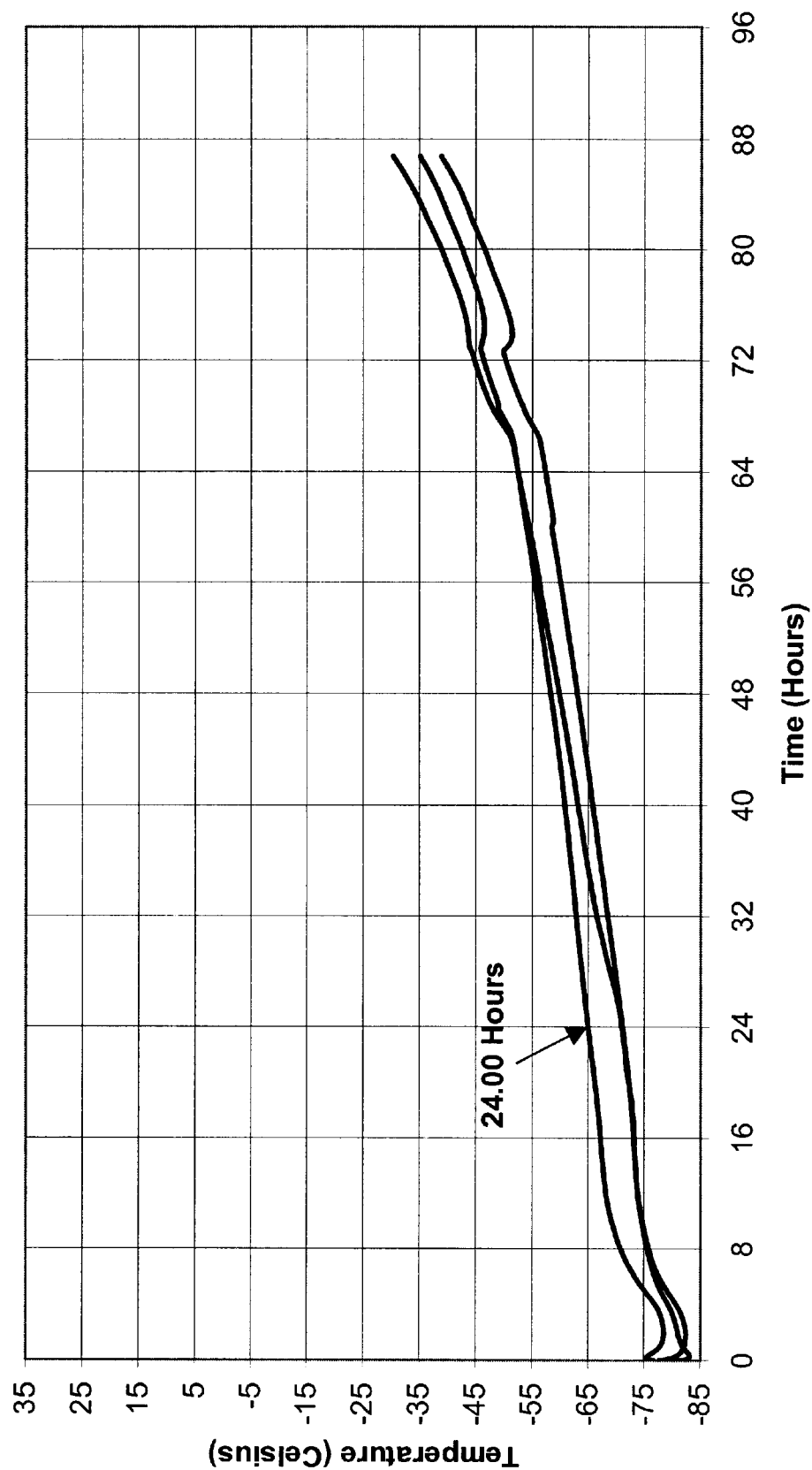
FIG. 7 is a graph showing temperature of products over time in a conventional shipping container laying on its side.

FIG. 7 shows the temperature of simulated products in a conventional shipping container laid on its side, with no spring assembly and no vacuum insulated panels. One piece of the simulated product exceeded the target temperature of −65° C. after only 24 hours in the conventional shipping container. The last piece of simulated product to exceed −65° C. did so after approximately 42 hours.

Design Test 2: Effect of Periodic Rotation

Figure 8:
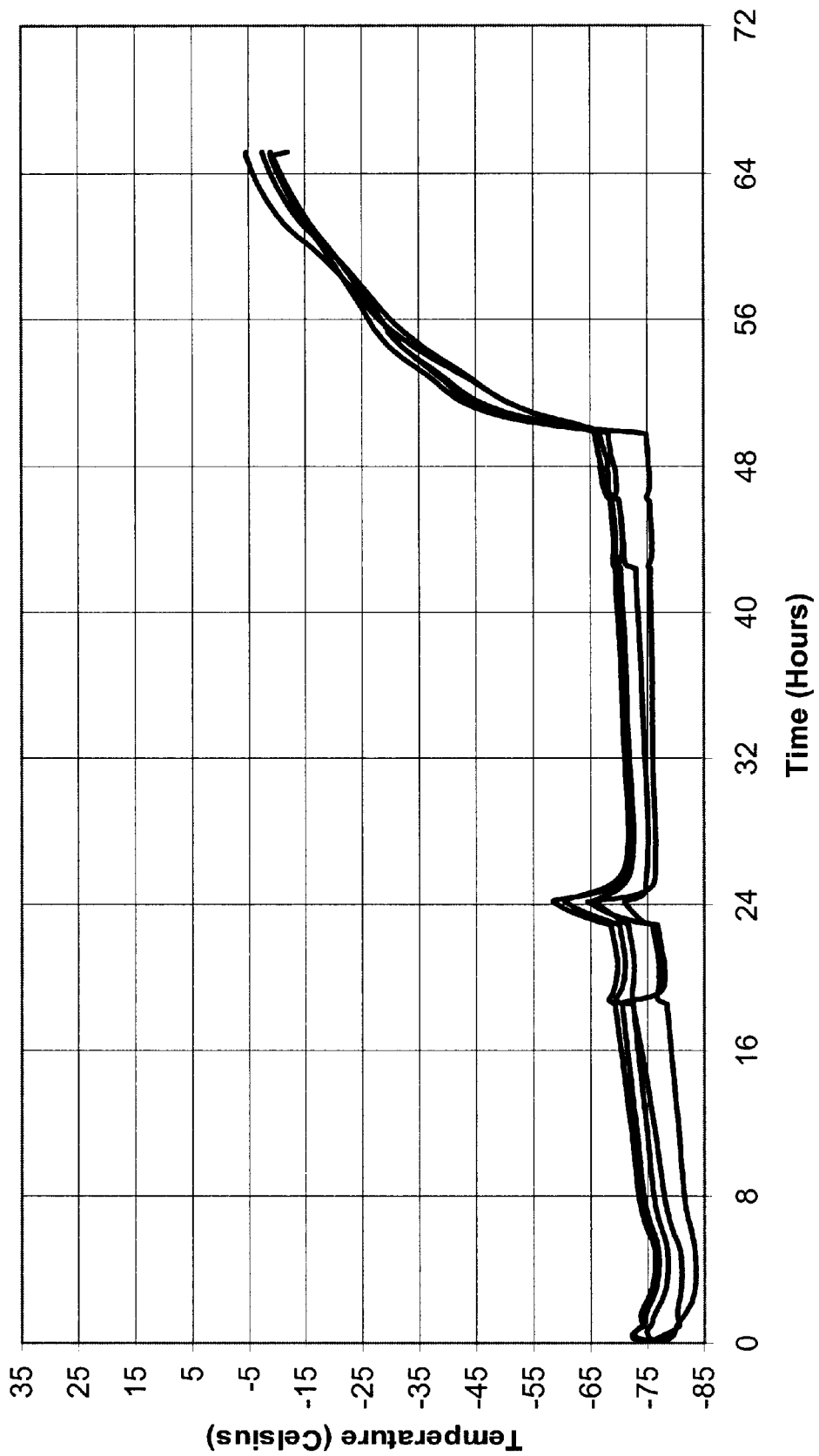
FIG. 8 is a graph showing temperature of products over time in a conventional shipping container, as the container is periodically rotated.

FIG. 8 shows the temperature of simulated products in the conventional shipping container as in Design Test 1, however the container was periodically rotated throughout this test, for example at 20 hours, 24 hours, 42 hours, 46 hours, and 50 hours. All pieces of the simulated product remained below −65° C. for approximately 50 hours, indicating that periodic rotation increased the performance of the conventional container for maintaining frozen products.

Design Test 3: Effect of Spring Assembly

Figure 9:
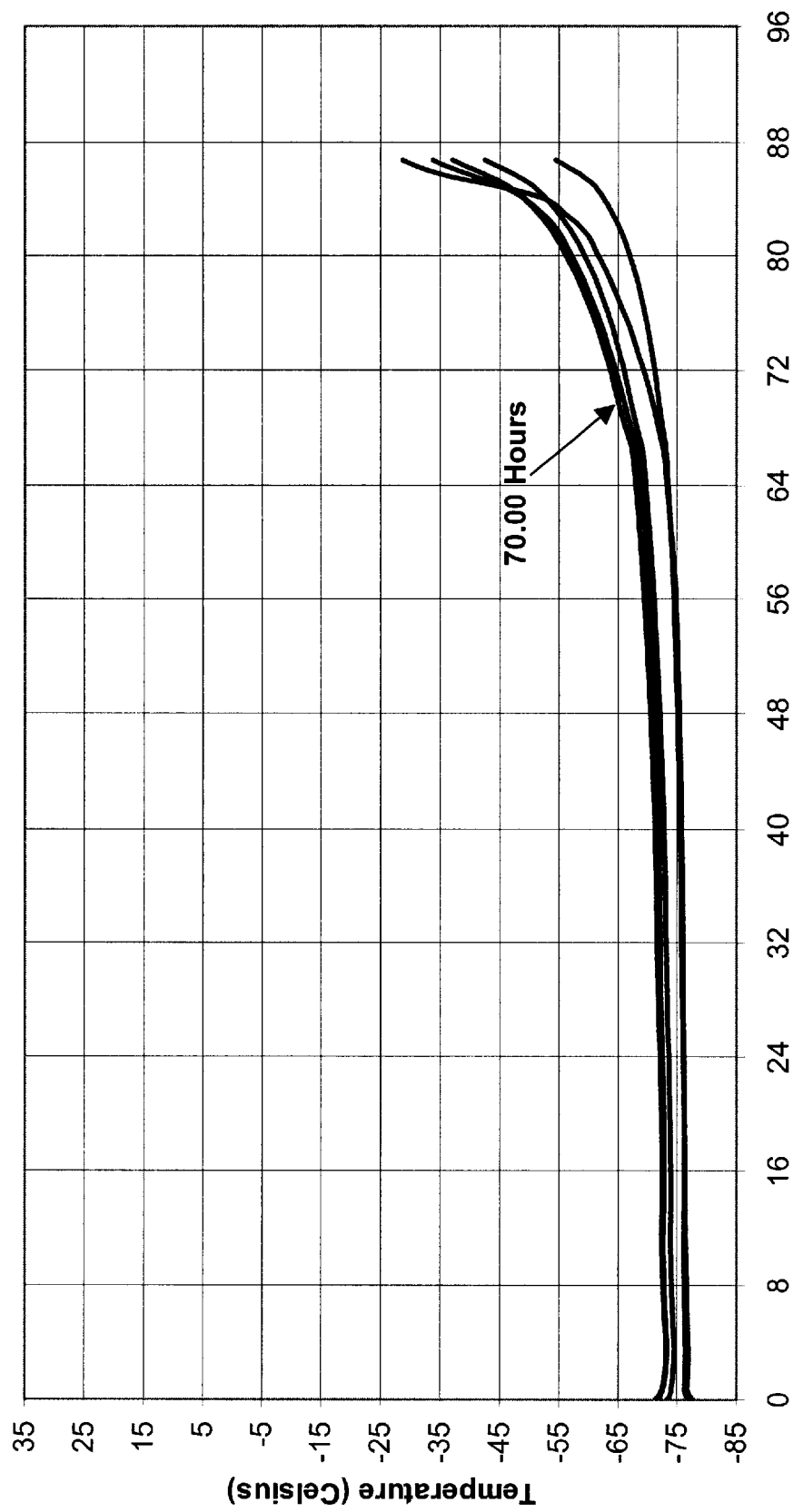
FIG. 9 is a graph showing temperature of products over time in a shipping container including a spring assembly according to the present invention.

FIG. 9 shows the temperature of simulated products in a container similar to the conventional container used in Design Tests 1 and 2, however the container used in Design Test 3 also included one spring assembly according to the present invention. As in Design Test 1, the container remained on its side for the entire duration of the test. As shown in FIG. 9, all products remained at or below −65° C. for at least 70 hours, with a maximum duration of approximately 80 hours. Thus, the spring assembly of the present invention dramatically improved the duration of effectiveness of the container by approximately 46 hours (e.g. from a minimum of 24 hours in Design Test 1 to at least 70 hours in Design Test 3).

Design Test 4. Effect of Spring Assembly + Vacuum Panels

Figure 10:
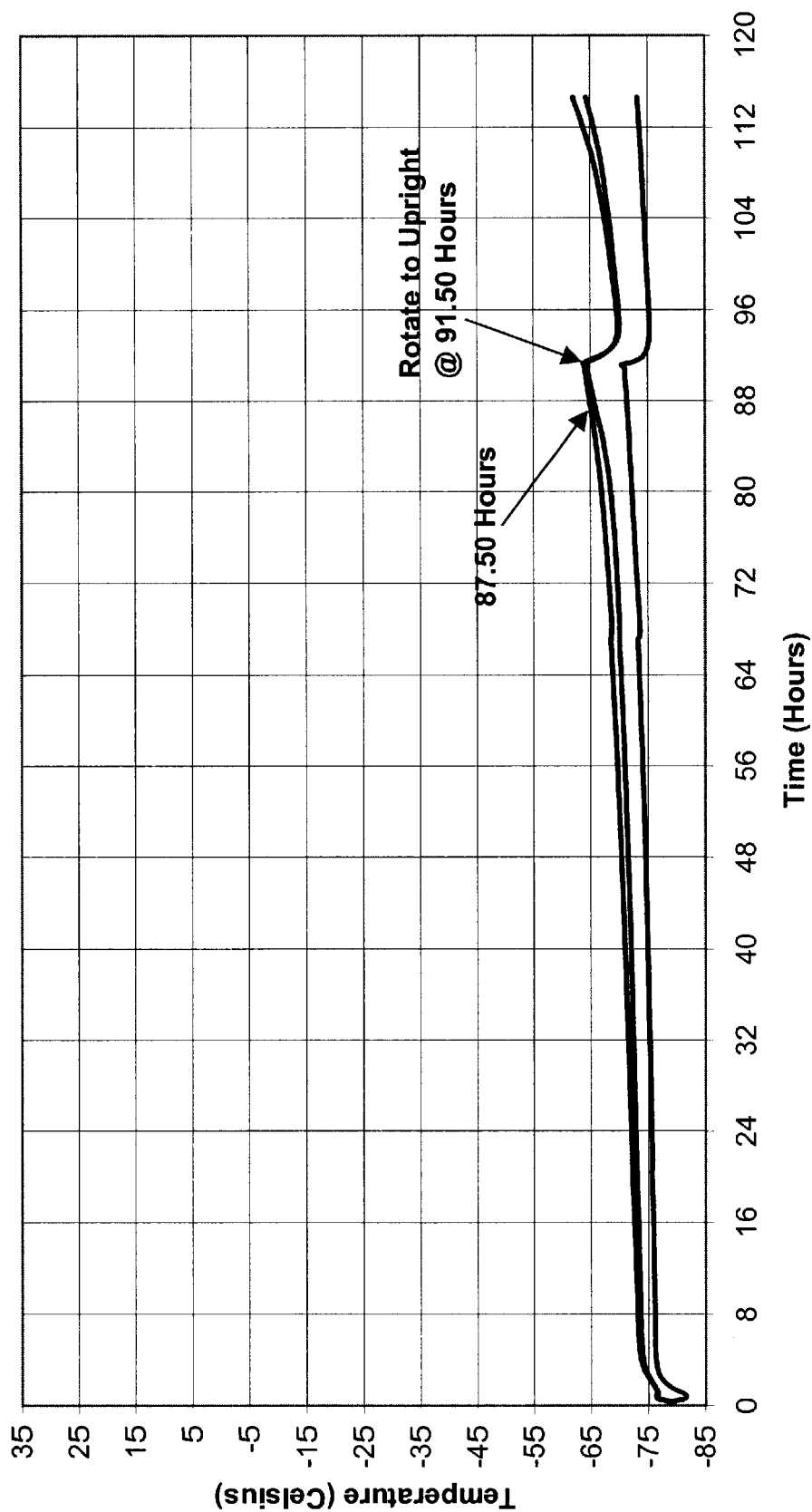
FIG. 10 is a graph showing temperature of products over time in a shipping container including a spring assembly and vacuum panels according to the present invention.

FIG. 10 shows the temperature of products in a shipping container having both a spring assembly and an inner container of vacuum panels according to the present invention. The temperature of the products, again shown in thick solid lines, remained at or below −65° C. for at least 87.5 hours with the container resting on its side. At 91.5 hours, the shipping container was rotated to upright, resulting in decreased temperatures in all products and further extending the duration below −65° C. to approximately 110 hours. Thus the combination of a spring assembly and insulated panels according to the present invention further increased the effectiveness of the container as compared with the spring assembly alone. Additionally, the decreased temperatures with rotation of the container suggests that periodic rotation or movement further increases the time that products may be maintained in such a container.

While the invention is susceptible to various modifications and alternative forms, specific examples thereof have been shown in the drawings and are herein described in detail. It should be understood, however, that the invention is not to be limited to the particular forms or methods disclosed, but rather the invention is to cover all modifications, equivalents and alternatives falling within the spirit and scope of the appended claims.

What is claimed is:

1. A container for shipping and storing frozen products, comprising:
    a body having a product chamber and an open end, the product chamber having a shape adapted to receive a product disposed between a first cooling element and a second cooling element;
    a lid assembly adapted to sealingly engage the open end of the body; and
    a first spring assembly positioned within said product chamber, said first spring assembly adapted to bias the first cooling element toward the second cooling element when the lid assembly engages the body, such that the product is held between the first cooling element and the second cooling element.

2. The container of claim 1, wherein said lid assembly includes a restraint for suspending the second cooling element therefrom when said lid assembly is removed from said body.

3. The container of claim 2, wherein the restraint is a net suspended from a bottom surface of said lid assembly, such that the net and the second cooling element enter the product chamber when said lid assembly engages said body.

4. The container of claim 1, wherein the body includes at least one side wall defining a side of the product chamber and a bottom lid defining a bottom of the product chamber opposite the open end.

5. The container of claim 4, wherein said side wall and said bottom lid are comprised of polystyrene.

6. The container of claim 4, wherein said first spring assembly is disposed between said bottom lid and the first cooling element.

7. The container of claim 6, further comprising a second spring assembly disposed in said product chamber between said lid assembly and the second cooling element when said lid assembly engages the open end of the body, such that the first and second cooling elements and the product are disposed between the first spring assembly and the second spring assembly.

8. The container of claim 4, wherein said first spring assembly is disposed between said lid assembly and the second cooling element when said lid assembly engages the open end of the body.

9. The container of claim 4, wherein said first spring assembly is disposed between said side wall and the first cooling element, such that said first spring assembly biases the first cooling element in a direction orthogonal to the open end of the body.

10. The container of claim 9, further comprising a second spring assembly disposed in said product chamber, said second spring assembly adapted to oppose the first spring assembly and bias the second cooling element toward the first cooling element.

11. The container of claim 4, wherein:
    said body further includes an inner container comprising at least one side panel disposed between said side wall and the product chamber and a bottom panel disposed between the bottom lid and the product chamber; and
    said lid assembly includes a lid panel adapted to sealingly engage said inner container when said lid assembly engages said body.

12. The container of claim 11, wherein said side panel, bottom panel, and lid panel are vacuum insulated panels.

13. The container of claim 12, further comprising:
    a bottom gasket disposed between a bottom edge of said side panel and said bottom panel; and
    a top gasket disposed between a top edge of said side panel and said lid panel when said lid panel sealingly engages said side panel.

14. The container of claim 11, further comprising a liner separating said product chamber from said inner container.

15. The container of claim 11, wherein said first spring assembly is disposed between said lid panel and the second cooling element when said lid assembly engages the open end of the body.

16. The container of claim 11, wherein said first spring assembly is disposed between said bottom panel and the first cooling element.

17. The container of claim 16, wherein said first spring assembly comprises a top plate, a bottom plate and a spring member attached to and disposed between said top and bottom plates, said top plate positioned toward the open end of said body and adapted to support the first cooling element.

18. The container of claim 17, wherein said top plate includes a locating clip adapted to hold said first cooling element in a position on said top plate.

19. The container of claim 18, further comprising:
    the first cooling element disposed in said product chamber on said top plate of said first spring assembly;
    the second cooling element disposed in said product chamber adjacent to said lid assembly; and
    the product disposed in said product chamber and held between the first cooling element and the second cooling element.

20. The container of claim 19, wherein said second cooing element is held within a restraint attached to said lid assembly, such that said second cooling element is removed from said product chamber when said lid assembly is removed from said body.

21. The container of claim 20, wherein said restraint is a net attached to said lid assembly, wherein a portion of said net contacts said product and is between said second cooling element and said product when said lid assembly engages said body.

22. The container of claim 1, further comprising a shipping carton into which the body is received.

23. The container of claim 1, wherein said product is maintained at or below a temperature of −65° C. in said container for at least 72 hours.

24. The container of claim 1, wherein said product is maintained at or below a temperature of −65° C. in said container for at least 96 hours.

25. The container of claim 1, wherein said product is maintained at or below a temperature of −65° C. in said container for at least 120 hours.

26. The container of claim 1, wherein the product is at least one frozen tissue.

27. A container for shipping and storing frozen products, comprising:
   an body having a product chamber and an open end,
   a lid assembly adapted to sealingly engage the open end of the body;
   at least one product disposed in said product chamber between a first cooling element and a second cooling element;
   a first spring assembly disposed in said product chamber, wherein said first spring assembly biases the first cooling element toward the second cooling element when the lid assembly engages the body, such that said product is held between the first cooling element and the second cooling element.

28. The container of claim 27, further comprising a plurality of products disposed between the first and second cooling elements.

29. The container of claim 27, wherein a restraint attaches said second cooling element to said lid assembly.

30. The container of claim 27, wherein said first spring assembly is disposed between said lid assembly and said second cooling element when said lid assembly engages the open end of the body.

31. The container of claim 27, wherein:
   said body comprise at least one side panel defining a side of the product chamber and a bottom panel defining a bottom of the product chamber opposite the open end; and
   said lid assembly comprises a lid panel configured to sealingly engage said side panel when said lid assembly engages the open end of the body.

32. The container of claim 31, wherein said side panel, bottom panel, and lid panel are vacuum insulated panels.

33. The container of claim 31, wherein said first spring assembly is disposed between said bottom panel and the first cooling element, such that said first spring assembly biases the first cooling element against the product and the product against the second cooling element.

34. The container of claim 33, wherein said first spring assembly comprises a top plate, a bottom plate and a spring member attached to and disposed between said top and bottom plates, said top plate positioned toward the open end of said body and supporting said first cooling element.

35. The container of claim 34, wherein said top plate includes a locating clip adapted to hold said first cooling element in a position on said top plate.

36. The container of claim 33, wherein said second cooing element is held within a restraint attached to said lid assembly, such that said second cooling element is removed from said product chamber when said lid assembly is removed from said body.

37. The container of claim 36, wherein said restraint is a net attached to said lid assembly, and wherein a portion of said net contacts said product and is between said second cooling element and said product when said lid assembly engages said body.

38. The container of claim 31, wherein said first spring assembly is disposed between said side panel and the first cooling element, such that said first spring assembly biases the first cooling element against the product in a direction orthogonal to the open end of said body.

39. The container of claim 38, further comprising a second spring assembly disposed in said product chamber, said second spring assembly adapted to oppose the first spring assembly and bias the second cooling element toward the first cooling element.

40. The container of claim 27, further comprising a shipping carton into which the body is received.

41. The container of claim 27, wherein said product is maintained at or below a temperature of −65° C. in said container for a duration of at least 72 hours.

42. The container of claim 27, wherein said product is maintained at or below a temperature of −65° C. in said container for at least 96 hours.

43. The container of claim 27, wherein said product is maintained at or below a temperature of −65° C. in said container for at least 120 hours.

44. The container of claim 27, wherein the product is at least one frozen tissue.

45. A container for shipping and storing frozen products, comprising:
   a body having an open end and a product chamber defined by at least one wall;
   a door assembly adapted to sealingly engage the open end of the body;
   at least one product disposed in said product chamber between a first cooling element and a second cooling element;
   a first spring assembly disposed in said product chamber between the first cooling element and the wall of the product chamber; and
   a second spring assembly disposed in said product chamber and adapted to bias the second cooing element toward the first cooling element, such that the product is held between the first and second cooling elements.

46. A container according to claim 45, wherein the product chamber is further defined by a second wall, and the second spring assembly is disposed between the second wall and the second cooling element.

47. The container of claim 46, wherein:
   the first spring assembly provides a first biasing force in a direction orthogonal to the open end of the body,
   the second spring assembly provides a second biasing force opposing the first biasing force, and
   the product is held between the first and second cooling elements by the first and second biasing forces.

48. The container of claim 45, further comprising a plurality of products disposed between the first and second cooling elements.

49. The container of claim 45, wherein:
   said body comprises at least one side panel lining the product chamber; and said door assembly comprises at least one door panel that sealingly engages the side panel when said door assembly engages said body.

50. The container of claim 45, wherein said side panel and said door panel are vacuum insulated panels.

51. The container of claim 45, wherein:
said first spring assembly comprises a first top plate, a bottom plate and a spring member attached to and disposed between said top and bottom plates, said top plate adjacent to said first cooling element.

52. The container of claim 51, wherein said top plate includes a locating clip adapted to hold said first cooling element in a position on said top plate.

53. The container of claim 45, further comprising a shipping carton into which the body is received.

54. The container of claim 45, wherein said product is maintained at or below a temperature of −65° C. in said container for a duration of at least 72 hours.

55. The container of claim 45, wherein said product is maintained at or below a temperature of −65° C. in said container for at least 96 hours.

56. The container of claim 45, wherein said product is maintained at or below a temperature of −65° C. in said container for at least 120 hours.

57. The container of claim 45, wherein said product is at least one frozen tissue.

* * * * *